United States Patent
Arunakumari et al.

(10) Patent No.: US 8,357,514 B2
(45) Date of Patent: Jan. 22, 2013

(54) METHODS OF GENE AMPLIFICATION AND EXPRESSION

(75) Inventors: Alahari Arunakumari, Pennington, NJ (US); Xiao-Ping Dai, Bloomsbury, NJ (US); Haile Ghebramariam, Easton, PA (US)

(73) Assignee: Medarex, Inc., Princeton, NJ (US)

( * ) Notice: Subject to any disclaimer, the term of this patent is extended or adjusted under 35 U.S.C. 154(b) by 203 days.

(21) Appl. No.: 12/593,132

(22) PCT Filed: Mar. 27, 2008

(86) PCT No.: PCT/US2008/058436
§ 371 (c)(1),
(2), (4) Date: Mar. 18, 2010

(87) PCT Pub. No.: WO2008/121711
PCT Pub. Date: Oct. 9, 2008

(65) Prior Publication Data
US 2010/0178673 A1    Jul. 15, 2010

Related U.S. Application Data

(60) Provisional application No. 60/908,529, filed on Mar. 28, 2007.

(51) Int. Cl.
*C12P 21/06* (2006.01)
*C12N 15/63* (2006.01)
(52) U.S. Cl. ................ 435/69.6; 435/455
(58) Field of Classification Search ............ None
See application file for complete search history.

(56) References Cited

U.S. PATENT DOCUMENTS

| 5,721,121 A | 2/1998 | Etcheverry et al. |
| 6,872,549 B2 | 3/2005 | Van Ness et al. |

FOREIGN PATENT DOCUMENTS

WO    WO 03/046162    6/2003

OTHER PUBLICATIONS

Wurn, F., "Production of recombinant protein therapeutics in cultivates mammalian cells." Nature Biotechnology, vol. 22, No. 11, pp. 1393-1398 (2004).
Kim et al., "Characterization of Chimeric Antibody Producing CHO Cells in the course of . . . " Biotechnology and Bioengineering, vol. 58, No. 1, pp. 73-84 (1998).
Ringold et al., "Co-expression and amplification of dihydrofolate reductase cDNA and the *Escherichia coli* . . . " J. Mol Appl Genet, vol. 1, No. 1, Abstract (1981).
Gray, D., "Overview of Protein Expression by Mammalian Cells", Current Protocols in Protein Science, pp. 5.9.1-5.9.18 (1997).
Peroni, C.N., et al., "High-level expression of human thyroid-stimulating hormone in Chinese hamster ovary cells by co-transfection of dicistronic expression vectors followed by a dual-marker amplication strategy", Biotechnol. Appl. Biochem., vol. 35, pp. 19-26 (2002).
Soares, C.R.J. et al., "High-level synthesis of human prolactin in Chinese-hamster ovary cells", Biotechnol. Appl. Biochem., vol. 32, pp. 127-135 (2000).

*Primary Examiner* — Kagnew H Gebreyesus
(74) *Attorney, Agent, or Firm* — Z. Angela Guo

(57) ABSTRACT

Disclosed are methods relating to amplification and expression of a nucleic acid sequence encoding a polypeptide of interest in recombinant cells, and cell lines and polypeptides produced from such methods. The methods disclosed herein permit the amplification of cell lines that express a polypeptide of interest in a relatively short period of time through the use of a bioreactor.

11 Claims, 9 Drawing Sheets

METHODS OF GENE AMPLIFICATION AND EXPRESSION

CROSS-REFERENCE TO RELATED APPLICATIONS

This application claims priority to U.S. Provisional Application Ser. No. 60/908,529 filed Mar. 28, 2007, which is hereby incorporated by reference in its entirety.

FIELD OF THE INVENTION

The present invention generally relates to methods of amplification and expression of a nucleic acid sequence encoding a polypeptide of interest in recombinant cells. The methods of the present invention provide amplified cell lines in a relatively short period of time through the use of a bioreactor.

BACKGROUND

Many commercially important polypeptides are produced in recombinant cells grown in culture. One method for producing such polypeptides involves the generation of an amplified cell line by transfection of host cells with two nucleic acid sequences, one of which encodes a polypeptide of interest, and another which encodes an amplifiable marker, such as dihydrofolate reductase (DHFR). In instances in which the amplifiable marker is DHFR, transfected cells are subjected to selective pressure by culturing the cells in increasing concentrations of the amplification agent methotrexate (MTX), as is well known in the art. The normally cytotoxic effects of MTX are substantially eliminated by expression of DHFR. Transfected cells are believed to survive because the DHFR gene has been integrated into the genome of the transfected cell. Increasing the DHFR copy number to a sufficiently high level through amplification enables the cell line to be resistant to higher levels of MTX. Similarly, as the nucleic acid sequence encoding DHFR is amplified, the nucleic acid sequence encoding the polypeptide of interest is also amplified, thereby increasing expression of that sequence.

However, this method of amplification and increased expression has drawbacks. In particular, the generation of most suitable recombinant cell lines utilizing this method is labor-intensive and can require several months to perform. For example, this amplification method has traditionally been performed in tissue culture flasks, shake flasks, or spinner flasks by subjecting a cell line with a low level of expression of the amplifiable marker to sequential step-wise increases in concentration of the amplification agent after maintaining the cells for several weeks. Thus, the time required to progress to the next stage can be several months. In addition, previous methods of amplification are typically labor-intensive because the cell lines must continuously be evaluated over several months to ensure that amplification is occurring.

Accordingly, it would be desirable to provide efficient methods for the amplification of cell lines that express a polypeptide of interest in a relatively short period of time.

SUMMARY

The present invention generally relates to methods of amplification of a nucleic acid sequence encoding a polypeptide of interest in recombinant cells. The methods of the present invention can provide amplified cell lines in a relatively short period of time through the use of a bioreactor.

In one embodiment, the present invention provides a method for producing a recombinant cell line that expresses a polypeptide of interest, comprising (a) culturing a host cell in a bioreactor in media, wherein the host cell is transfected with (i) a nucleic acid sequence encoding a polypeptide of interest and (ii) a nucleic acid sequence encoding an amplifiable marker; and (b) adding an increasing amount of an amplification agent to the media to produce the recombinant cell line.

In another embodiment, the present invention provides a method for producing a recombinant cell line that expresses a polypeptide of interest, comprising culturing a host cell in a bioreactor, wherein the host cell has been transfected with a nucleic acid sequence encoding a polypeptide of interest and a nucleic acid sequence encoding an amplifiable marker, in media containing increasing amounts of an amplification agent, and thereby amplifying the nucleic acid sequence encoding the amplifiable marker.

In another embodiment, the present invention provides a method for producing a polypeptide of interest, which comprises culturing a host cell transfected with (i) a nucleic acid sequence encoding a polypeptide of interest and (ii) a nucleic acid sequence encoding an amplifiable marker in a bioreactor in media containing increasing amounts of an amplification agent, thereby expressing the polypeptide of interest.

In yet another embodiment, the present invention provides a method for producing a polypeptide of interest, comprising culturing a host cell in a bioreactor, wherein the host cell has been transfected with a nucleic acid sequence encoding a polypeptide of interest and a nucleic acid sequence encoding an amplifiable marker, in media containing increasing amounts of an amplification agent, and thereby amplifying the nucleic acid sequence encoding the amplifiable marker and expressing the polypeptide of interest.

The features and advantages of the present invention will be readily apparent to those skilled in the art. While numerous changes can be made by those skilled in the art, such changes are within the spirit of the invention.

BRIEF DESCRIPTION OF THE DRAWINGS

These drawings illustrate certain aspects of some of the embodiments of the present invention, and are not intended to be limiting.

DETAILED DESCRIPTION

Figure 1:
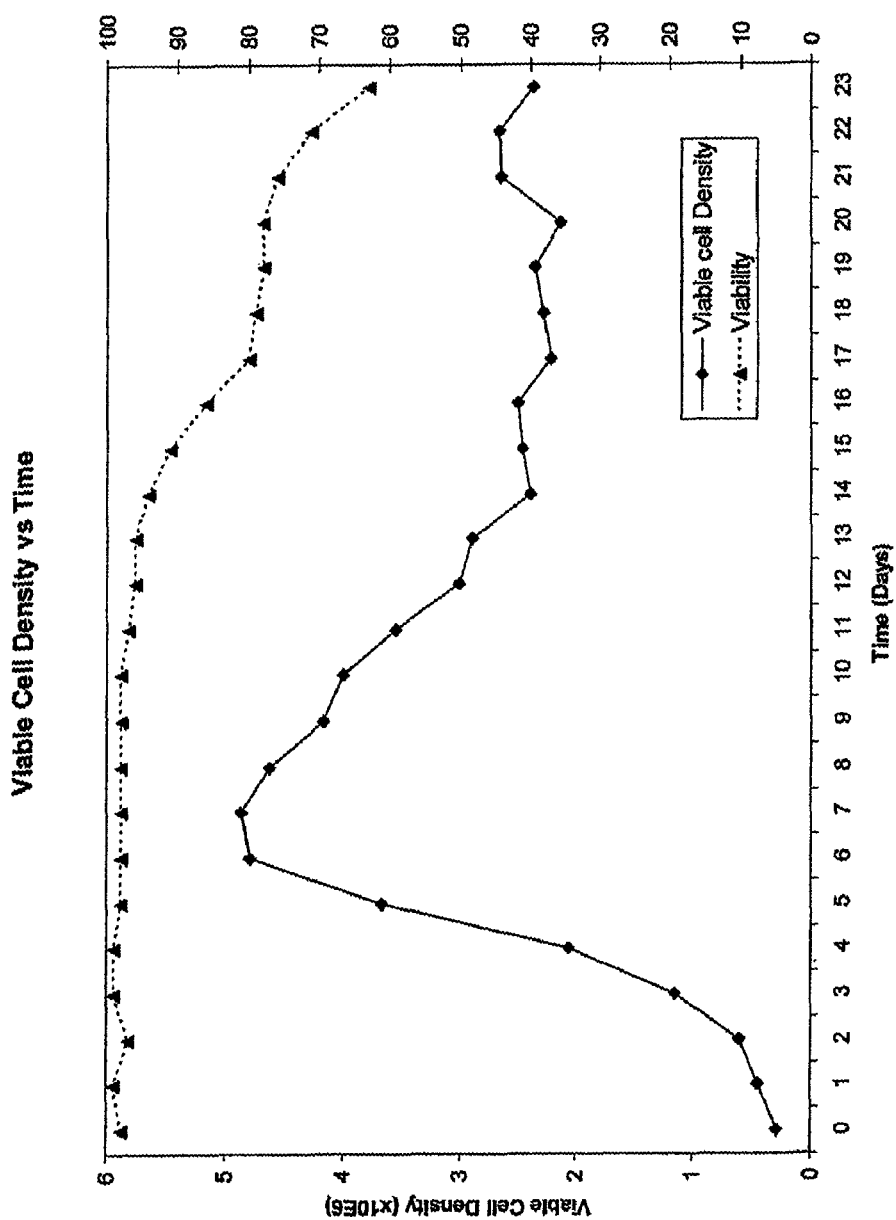
FIG. 1 is a graph illustrating the viability and density of recombinant cells amplified in a bioreactor in accordance with the methods of the present invention.

The present invention provides efficient methods of amplification and expression of a nucleic acid sequence encoding a polypeptide of interest in recombinant cells, and cell lines and polypeptides produced from such methods. The methods of the present invention can provide amplified cell lines in a relatively short period of time through the use of a bioreactor.

A particular advantage of the present invention is that it allows for amplified cell lines to be developed much more rapidly than was previously possible using existing step-wise amplification procedures. In addition, the instant methods are less labor-intensive because the cell lines do not need to be continuously monitored over a lengthy period of time to verify that amplification is occurring. The savings in time is realized, in part, by the use of a bioreactor according to the amplification process of the present invention. Furthermore, an additional advantage is that the amplified cell lines produced in the present invention can be better adapted for subsequent culturing in a bioreactor. Without intending to be limited to any particular mechanism of action, it is believed that this advantage is realized in performing the instant method, at least in part, because the amplified cells have already experienced the shear stress associated with bioreactor culture conditions.

According to the present invention, a host cell is transfected with two nucleic acid sequences, one encoding a polypeptide of interest and another encoding an amplifiable marker. A cell has been "transfected" when an exogenous nucleic sequence has been introduced inside the cell membrane and permanent (i.e., stable) transformation of a nucleic acid sequence occurs. The host cell is then cultured in a bioreactor in media containing increasing amounts of an amplification agent. The host cells are monitored for cell viability and/or cell density to determine, inter alia, if amplification is occurring and/or when the amount of the amplification agent can be increased. In general, cell viability is the primary indicator used in determining when the amount of an amplification agent can be increased. When percent cell viability is increasing or stable (i.e., viability+/−10%) based upon two or more consecutive measurements, the concentration of the amplification agent can be elevated in accordance with the method of the invention. When percent cell viability is declining (i.e., viability>10% decline) continuously, the amplification agent concentration is not increased. Any conventional method for measuring percent cell viability can be used for this purpose, e.g., dye (Trypan-Blue) exclusion method. The culture can be monitored on a daily basis or more frequently if desirable to determine the % cell viability. Generally, amplification is thought to be occurring when a decrease in cell viability and/or cell density is observed, followed by a subsequent increase in cell viability and/or density.

Cells can be monitored for viability and/or density through a variety of methods, including, but not limited to manual methods or automated methods that utilize dye exclusion techniques. One of ordinary skill in the art with the benefit of this disclosure will recognize other suitable methods of monitoring cell viability and/or cell density. Once the cells have reached the desired cell viability and/or density in the desired concentration of the amplification agent, the amplified cell line can then be used to produce a desired amount of the polypeptide of interest.

Through the use of a bioreactor, the present invention provides methods wherein amplification of a particular nucleic acid sequence, and subsequent expression of a polypeptide of interest, can be achieved at an increased rate relative to cells not selected in a bioreactor. In some embodiments, the present invention can allow for a reduction in the amount of time necessary to produce an amplified cell line by about 25%. In other embodiments, the present invention can allow for a reduction in the amount of time necessary to produce an amplified cell line by about 50%. In yet another embodiment, the present invention can allow for a reduction in the amount of time necessary to produce an amplified cell line by about 60%. In the absence of any other rate enhancing procedures, the present invention can allow for the production of an amplified cell line in approximately two to three months.

Host cells used in a method of the present invention are cultured in a bioreactor according to standard cell culture techniques. As used herein, the term "bioreactor" refers to a continuous culture device used to grow cells. Any bioreactor suitable for culturing cells, particularly for producing large quantities of a protein of interest on a commercial scale, can be used in a method of the present invention, including, for example, fed-batch, perfusion, stirred tank, airlift, and disposable bioreactors. As those of ordinary skill in the art will appreciate, the type of bioreactor used in a method of the invention is not critical, provided it is capable of culturing the host cells, and one can select the particular bioreactor based on production needs. In one embodiment of the present invention, the bioreactor is a perfusion bioreactor.

Host Cells and Preparation

The methods disclosed herein are suitable for use with a wide variety of host cells. More specifically, any cell type capable of being cultured in a bioreactor can be used in the present invention as a host cell. However, as one of ordinary skill in the art with the benefit of this disclosure will realize, the present invention can be particularly suitable for use with eukaryotic host cells, which can take a longer period of time to amplify, so that the advantage of the reduction in time can be recognized.

The term "host cells" as used herein refers to cells that have been transfected with a nucleic acid sequence encoding a polypeptide of interest and a nucleic acid sequence encoding an amplifiable marker. In some embodiments, host cells can be transfected with a vector comprising a nucleic acid sequence encoding a polypeptide of interest and a nucleic acid sequence encoding an amplifiable marker. The phrases "nucleic acid sequence encoding a polypeptide" and "nucleic acid sequence encoding an amplifiable marker" as used herein refer to nucleic acid molecules which can be transcribed and translated in vivo when placed under the control of appropriate regulatory nucleic acids. The boundaries of the coding sequence are determined by a start codon at the 5' (amino) terminus and a translation stop codon at the 3' (carboxy) terminus. A coding sequence can include, but is not limited to, DNA, RNA, mRNA, cDNA, genomic DNA, and analogs thereof from prokaryotes, eukaryotes and synthetic sources. A transcription termination sequence is typically located 3' to the coding sequence. Those having ordinary skill in the art can select a particular host cell line which is capable of being cultured in a bioreactor and that is suited for expressing the polypeptide of interest.

In one embodiment, the host cells utilized in the present invention includes mammalian cells and cell lines and cell cultures derived therefrom. Mammalian cells, e.g., germ cells or somatic cells, can be derived from mammals, such as mice, rats, or other rodents, or from primates, such as humans or monkeys. It shall be understood that primary cell cultures or immortalized cells can be employed in carrying out the techniques of this invention.

In particular embodiments, the cell type is mammalian in origin including, but not limited to, Chinese hamster ovary (CHO) (e.g., DG44 and DUXB11; Urlaub, et al., Somatic Cell and Molecular Genetics 12:555-566 (1986); Haynes, et al., Nucleic Acids Research 11:687-706 (1983); Lau, et al., Molecular and Cellular Biology 4:1469-1475 (1984); Kaufman, Randal J., Methods in Enzymology 185:537-566 (1991), Chinese hamster fibroblast (e.g., R1610), human cervical carcinoma (e.g., HELA), monkey kidney line (e.g., CVI and COS), murine fibroblast (e.g., BALBc/3T3), murine myeloma (NS0; SP2/O), hamster kidney line (e.g., HAK), murine L cell (e.g., L-929), human lymphocyte (e.g., RAJI), human kidney (e.g., 293 and 293T). Host cell lines are typically commercially available (e.g., from BD Biosciences, Lexington, Ky.; Promega, Madison, Wis.; Life Technologies, Gaithersburg, Md.) or can be obtained from the American Type Culture Collection (ATCC, Manassas, Va.).

A nucleic acid sequence encoding a polypeptide of interest and a nucleic acid sequence encoding an amplifiable marker can be introduced or transfected into an appropriate host cell by various techniques well known in the art (see, e.g., Ridgway, 1973, Vectors: Mammalian Expression Vectors, Chapter 24.2, pp. 470-472, Rodriguez and Denhardt eds., Butterworths, Boston, Mass.; Graham, et al., Virology 52:456 (1973); Sambrook, et al., Molecular Cloning: A Laboratory Manual, Cold Spring Harbor Laboratories, New York (1989); Davis, et al., Basic Methods in Molecular Biology, Elsevier (1986); and Chu, et al., Gene 13:197 (1981)). The terms "transformation," "transfection," and "transduction," and their grammatical variations refer to the uptake of foreign nucleic acid by a cell by any means practicable. A cell has been "transfected" when an exogenous nucleic acid sequence has been introduced inside the cell membrane and permanent (i.e., stable) transfection of a nucleic acid sequence occurs. This is accompanied by integration of the transfecting nucleic acid sequence into the cellular genome by recombination. The means by which the uptake is accomplished can include transfection (including electroporation), transformation, protoplast fusion, calcium phosphate precipitation, cell fusion with enveloped DNA, microinjection, and infection with intact virus. Even transient expression at higher than normal levels is useful for functional studies or for the production and recovery of polypeptides of interest.

The term "recombinant," as used herein to describe a nucleic acid sequence, means a nucleic acid sequence that comprises a polynucleotide of genomic, cDNA, semisynthetic, or synthetic origin, which by virtue of its origin or manipulation (1) is not associated with all or a portion of the polynucleotide with which it is associated in nature, and/or (2) is linked to a polynucleotide other than that to which it is linked in nature. The term "recombinant," as used herein to describe a protein or polypeptide means a polypeptide produced by expression of a recombinant nucleic acid sequence. The term "recombinant," as used herein in reference to cells, means cells that can be or have been used as recipients for recombinant nucleic acid sequences, and include progeny of the original cell. It shall be understood that progeny of a single parental cell may not be completely identical in morphology or in genomic or total nucleic acid complement to the original parent, due to accidental or deliberate mutation. Progeny of a parental cell that are sufficiently similar to the parent to be characterized by a relevant property, such as the presence of a nucleic acid sequence encoding a desired polypeptide, are also considered progeny.

Suitable Vectors

In one embodiment, a nucleic acid sequence encoding a polypeptide of interest and a nucleic acid sequence encoding an amplifiable marker can be introduced into a host cell through the use of a vector. The term "vector" as used herein refers to any nucleic acid, preferably DNA, which is capable of directing the expression of a polypeptide of interest and which can transfer nucleic acid sequences to a host cell, and therefore includes a promoter, which is operably linked to the nucleic acid sequence for which expression is desired. In addition to components of the vector which may be required for expression of a nucleic acid sequence, suitable vectors can also include a bacterial origin of replication, additional amplifiable genes, a signal sequence allowing the vector to exist as single-stranded DNA (e.g., M13 origin of replication), a multiple cloning site, and/or a mammalian origin of replication (e.g., a SV40 or adenovirus origin of replication).

A nucleic acid sequence encoding a polypeptide of interest and a nucleic acid sequence encoding an amplifiable marker can be incorporated into a number of suitable vectors to facilitate introduction of a nucleic acid sequence encoding a polypeptide of interest and a nucleic acid sequence encoding an amplifiable marker into a host cell. Suitable vectors can be of any type including cloning, expression, and from any source, including viral. In one embodiment, the vector is a mammalian expression vector.

A vector suitable for use in the present invention typically includes one or more elements for means of replication, e.g., origin of replication, which can be episomal or chromosomal. Preferably, the replication sequence renders the vector capable of both means, such that the vector is capable of self-replication as an extrachromosomal unit and of integration into the chromosome, either due to the presence of a translocatable sequence, such as an insertion sequence or transposon, due to substantial homology with a sequence present in the chromosome or due to non-homologous recombinational events. The replication sequence or replicon will be one recognized by the transformed host and is derived from any source, such as from a plasmid, virus, the host cell, e.g., an autonomous replicating segment, by itself, or in conjunction with a centromere, or the like. The particular replication sequence is not critical to the subject invention and various sequences can be employed. Conveniently, a replication sequence of a virus can be employed.

Suitable vectors and methods for their preparation are well known in the art (see, e.g., Maniatis et al., supra), or they can be obtained through a commercial vendor, e.g., Invitrogen (Carlsbad, Calif.), Promega (Madison, Wis.), and Statagene (La Jolla, Calif.) and modified as needed. Examples of commercially available vectors include pcDNA3 (Invitrogen); pCMV-Script (Stratagene); and those disclosed in U.S. Patent App. No. 2005/0153394, the relevant disclosure of which is herein incorporated by reference.

Amplifiable Markers and Amplification Agents

As used herein, the term "amplifiable marker" refers to a marker utilized to select host cells that have amplified a particular nucleic acid sequence. Amplifiable markers are well-known in the art, and can be chosen for use in the invention to isolate stable transfectants based on the particular expression system desired by the skilled practitioner.

As used herein, the term "amplification agent" refers to a substance that interferes with the growth or survival of a host cell that is deficient in a particular amplifiable marker or a nucleic acid sequence encoding a particular amplifiable marker. Accordingly, a host cell that is transfected with a nucleic acid sequence encoding an amplifiable marker will be capable of growth or survival in the presence of a particular amplification agent whereas a nontransfected host cell would not be capable of growth or survival.

Any suitable nucleic acid sequence encoding an amplifiable marker can be used in the present invention. Typically, the nucleic acid sequence encoding an amplifiable marker that can be employed in this invention can be obtained from readily available sources. Examples of amplifiable markers and their amplification agents are provided in Table 1. See also Taylor and Feyereisen, Molecular Biology and Evolution, 13(6):719-734 (1996); and Kaufman, Methods in Enzymology, 185:537-566 (1990).

TABLE 1

| Amplification Agent | Amplifiable Marker |
| --- | --- |
| Methotrexate | Dihydrofolate reductase |
| Cadmium | Metallothionein |
| PALA | CAD (carbamoyl-P-synthetase, aspartate transcarbamylase, dihydroorotase) |
| Xyl-A-or adenosine and 2'-deoxycoformycin | Adenosine deaminase |
| Adenine, azaserine, and coformycin | Adenylate deaminase |
| 6-Azauridine, pyrazofuran | UMP Synthetase |
| Mycophenolic acid | IMP 5'-dehydrogenase |
| Mycophenolic acid with limiting xanthine | Xanthine-guanine phosphoribosyltransferase |
| Hypoxanthine, aminoopterin, and thymidine | Mutant HGPRTase or mutant thymidine kinase |
| 5-Fluorodeoxyuridine | Thymidylate synthetase |
| Multiple drugs e.g. adrimycin, vincristine or colchicine | P-glycoprotein 170 |
| Aphidicolin | Ribonucleotide reductase |
| Methionine sulfoximine | Glutamine synthetase |
| β-Aspartyl hydroxamate or Albizziin | Asparagine synthetase |
| Canavanine | Arginosuccinate synthetase |
| α-Difluoromethylornithine | Ornithine decarboxylase |
| Compactin | HMG-CoA reductase |
| Tunicamycin | N-Acetylglucosaminyl transferase |
| Borrelidin | Threonyl-tRNA synthetase |
| Ouabain | $Na^+K^+$-ATPase |

The appropriate concentration of the selection agent will vary based on the manner in which it is used. The parameters for such use can be readily ascertained by one having ordinary skill in the art. Cell lines deficient in genes encoding the amplifiable marker are also well-known in the art.

In one embodiment, DHFR is used as the amplifiable marker to allow for increased expression of the polypeptide of interest. DHFR is necessary for purine biosynthesis and, in the absence of exogenous purines, DHFR is required for growth of cells. Methotrexate (MTX) is a potent competitive inhibitor of DHFR, so increasing MTX concentration selects for cells that express increased levels of DHFR. The amplification methods of the present invention allow for the isolation of stably amplified cells that contain the amplified DHFR genes, as well as the polypeptide of interest, within their chromosomes. For uses of DHFR and MTX for gene amplification, see Maniatis, et al., Molecular Cloning, A Laboratory Manual, Cold Spring Harbor, Cold Spring Harbor, N.Y. (1992).

Polypeptide of Interest

A "polypeptide of interest" is any polypeptide for which increased production is desired. The present invention can be used to express a "heterologous" polypeptide of interest. As used herein, the term "heterologous" means a polypeptide that originates from a foreign species, or that is substantially modified from its original form if from the same species. Furthermore, an unmodified polypeptide that is not normally expressed in a cell is considered heterologous. Suitable polypeptides of interest can include any monomeric, dimeric or multimeric polypeptides. In addition, such polypeptides can be of the family of CXC chemokines and their receptors, CC chemokines and their receptors, CD proteins, interleukins and their receptors, interferons and their receptors, TNF super family and their receptors, and tumor-associated antigens which may not fall within any of the foregoing families of polypeptides. Furthermore, the polypeptide of interest can be an antibody, e.g., one that binds to any of the foregoing polypeptides.

Non-limiting examples of polypeptides of interest include: growth hormones such as human growth hormone, bovine growth hormone, parathyroid hormone, thyroid stimulating hormone, follicle stimulating hormone growth, luteinizing hormone, and hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); IL-8; chemerin; IP-10; CCL22; IL-23; SDF-1; IFN alpha; IL33; HIG2; IL-18; a serum albumin such as human serum albumin; mullerian-inhibiting substance; relaxin A- or B-chain; prorelaxin; mouse gonadotropin-associated peptide; IgE; Ig-Kappa; Ig-Lambda; DNase; inhibin; activin; receptors for hormones, growth factors, chemokines and cytokines, such as Neuropilin-1, CXCR4, IFNAR1, IL23R, ChemR23, CCR4, Folate receptor/FLR4, Frizzled-7, Frizzled-10, GITR, CXCR1, CXCR3, IL-18R; integrins, adhesion molecules, and their ligands, such as CD11a, CD11b, CD11c, CD18, an ICAM, Beta-4-integrin, VAP-1, VLA-4 and VCAM; protein A or D; rheumatoid factors; a neurotrophic factor such as bone-derived neurotrophic factor (BDNF), neurotrophin-3, -4, -5, or -6 (NT-3, NT-4, NT-5, or NT-6), growth factors including vascular endothelial growth factors (VEGF), nerve growth factor such as NGF-beta; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-beta-1, TGF-beta-2, TGF-beta-3, TGF-beta-4, or TGF-beta-5; insulin-like growth factor-I and -II (IGF-I and IGF-II); des(1-3)-IGF-I (brain IGF-1), insulin-like growth factor binding proteins; leukocyte surface markers, such as CD3, CD4, CD8, CD19, CD21, CD22, CD25, CD30, CD70, CD200, Lag 3, BTLA, IRTA1, IRTA2, IRTA3, IRTA4, IRTA5, CEACAM1, NKG2D, PD-1; Fc receptors, including CD16, CD32, CD64, CD89 and FcRn; erythropoietin; osteoinductive factors; OSCAR; OSCAR-ligand; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-1033; superoxide dismutase; T-cell receptors; a cytotoxic T-lymphocyte associated antigen (CTLA), such as CTLA-4; B7 family of proteins, including B7-H1, B7-H3, B7-H4 and B7-DC (PD-L2); tumor associated antigens such as HER2 receptor, HER3 receptor, HER4 receptor, RG-1, hCG, prostate specific membrane antigen (PSMA) receptor, Galectin-1, Galectin-3, Ephrin B3R, Fucosyl GM1, Edge4, Ptk7, Muc1, Mesothelin, Glypican 3, MICA, Fibronectin EDB, Testisin, Autotaxin, Hepsin, GPR56, KCNB, GPCR3, IGSF4, KIAA 1455, matriptase, Nucleolin, TMPRSS4, NGEP, PSGR, TF Antigen, RAET1G; decay accelerating factor; viral antigen such as, for example, a portion of the AIDS or SARS envelopes; transport proteins; homing receptors; addressins; regulatory proteins; enzymes; chimeric proteins such as immunoadhesins and fragments of any of the above-listed polypeptides. Examples of bacterial polypeptides or proteins include, e.g., Anthrax PA, C. difficile toxins A and B, SLT, alkaline phosphatase and beta-lactamase.

In one embodiment, the polypeptide of interest can be an antibody, which can be of any antibody type, e.g., murine, chimeric, humanized and human, or a combination thereof. A DNA sequence encoding an antibody can encode only a fragment of the antibody, e.g., the antigen binding portion or Fc portion, or a combination of both. Those of ordinary skill in the art will appreciate the term "antigen-binding portion" of an antibody refers to one or more fragments of an antibody that retain the ability to bind to an antigen. It has been shown that the antigen-binding function of an antibody can be performed by fragments of a full-length antibody. Examples of binding fragments encompassed within the term "antigen-binding portion" of an antibody include but are not limited to: (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward, et al., Nature 341:544-546 (1989)), which consists of a $V_H$ domain; and (vi) an isolated complementarity determining region (CDR). Furthermore, although the two domains of the Fv fragment, $V_L$ and $V_H$, are coded for by separate DNA sequences, they can be joined, using recombinant methods, by a synthetic linker that enables them to be made as a single protein chain in which the $V_L$ and $V_H$ regions pair to form monovalent molecules (known as single chain Fv (scFv); see e.g., Bird, et al., Science 242:423-426 (1988); and Huston, et al., Proc. Natl. Acad. Sci. USA 85:5879-5883 (1988)). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

Recombinant cells of the present invention are grown under conditions appropriate for the production of the polypeptide of interest, and assays can be performed to identify the encoded polypeptide of interest. Exemplary assay techniques for identifying and quantifying polypeptides include enzyme-linked immunosorbent assay (ELISA), radioimmunoassay (RIA), fluorescence-activated cell sorter analysis (FACS), immunohistochemistry, biacore analysis, homogeneous time-resolved fluorescence analysis (HTRF), and the like.

EXAMPLES

The present invention is also described by means of the following examples. However, the use of these or other examples anywhere in the specification is illustrative only and in no way intended to limit the scope and meaning of the invention or of any exemplified term. Likewise, the invention is not limited to any particular embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

A CHO cell line (clone #28) transfected with a nucleic acid sequence encoding human IgG and a nucleic acid sequence encoding the amplifiable marker DHFR was inoculated into a five liter perfusion bioreactor in animal component free medium comprising 500 nanomolar ("nM") of the amplification agent MTX. At the time of inoculation, the cell line expressed approximately 280 milligrams per liter ("mg/L") human IgG (12.116 p/c/d specific productivity). After 6 days, the concentration of the amplification agent, MTX, in the medium was increased from 500 nM to 1000 nM. After 11 days, the concentration of the amplification agent MTX in the medium was increased from 1000 nM to 2000 nM. After 22 days, the cells were harvested at $2.37 \times 10^6$ viable cells/mL and 63% viability. See FIG. 1.

These cells were then inoculated into spinner flasks to achieve actively growing cells at high viability (>90%) to subclone the cells at 0.5 cell/well.

Figure 2:
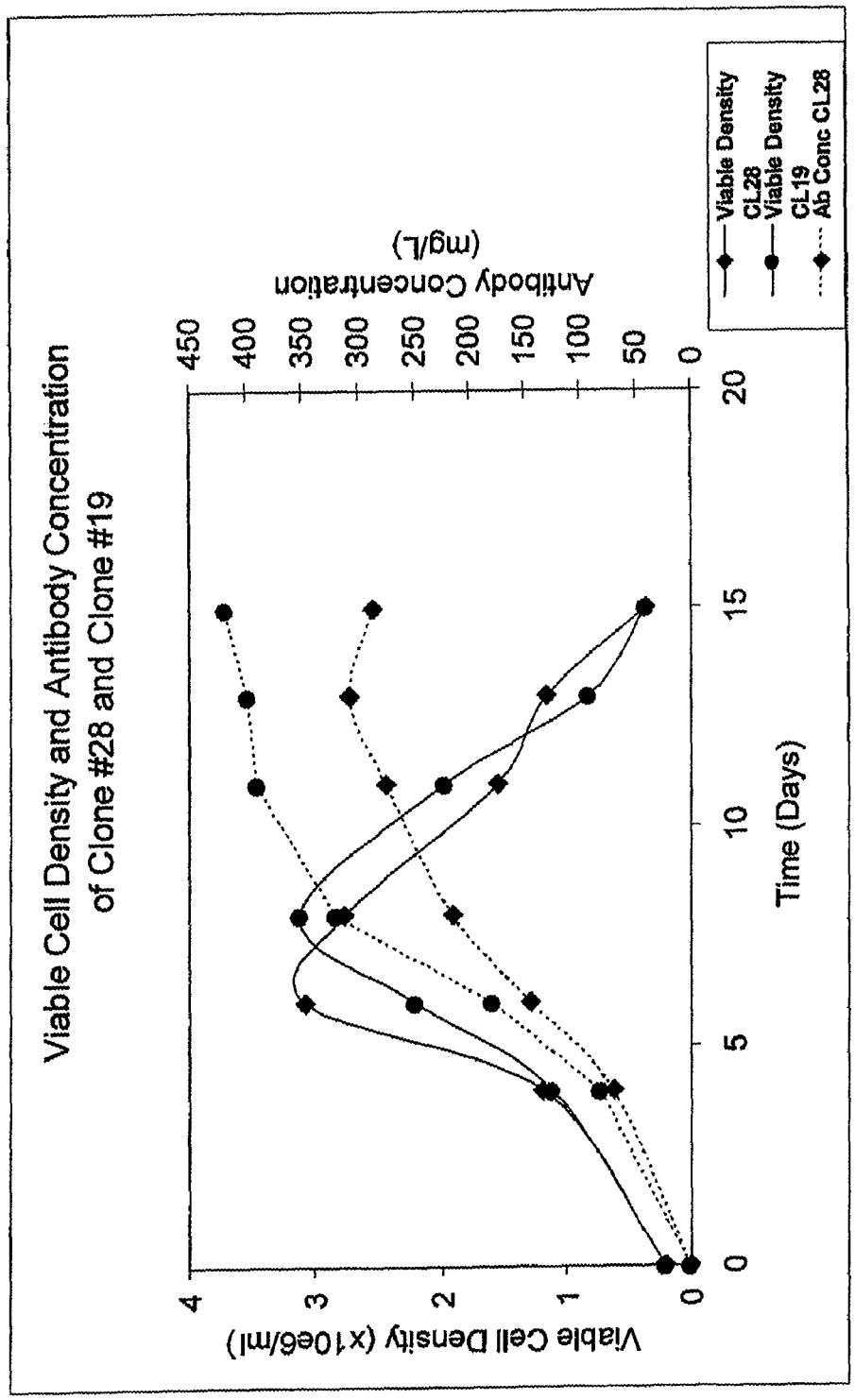
FIG. 2 is a graph illustrating the cell growth and expression level from perfusion amplified cell line (Clone #19) and pre-amplified cell line (Clone #28).
Figure 3:
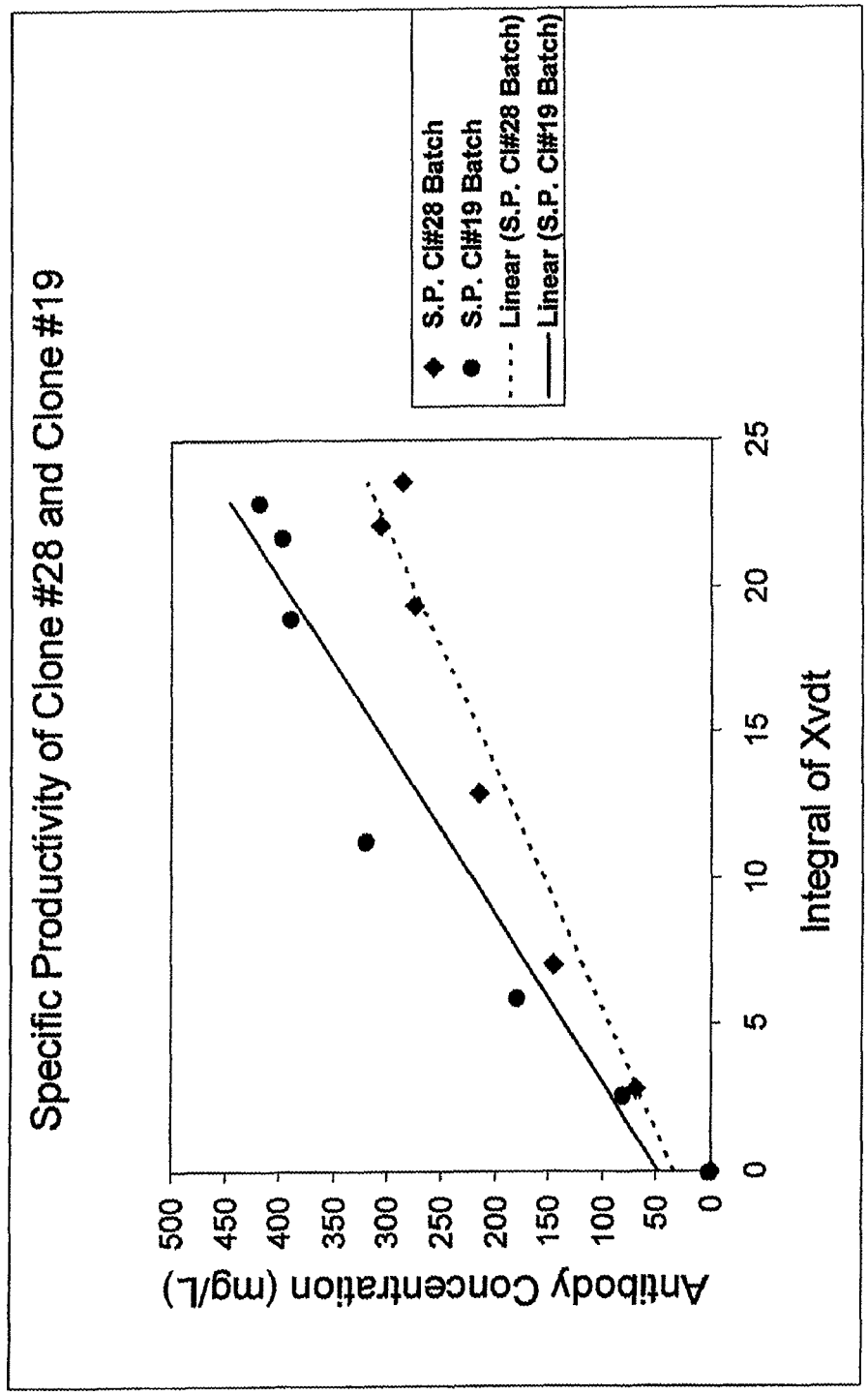
FIG. 3 is a graph illustrating the specific productivity from perfusion amplified cell line (Clone #19) and pre-amplified cell line (Clone #28).

After 28 days of incubation in 96 well plates, 80 single cell originating colonies were available for screening. Supernatants from the selected clones were assayed for human IgG content to identify the highest IgG expressing clones. Top antibody expressing clones were selected and transferred to 24 well plates for further evaluation. The top 8 antibody expressing clones from the 24 well plate were then expanded into T25 flasks for growth and productivity comparison. Out of the 8 clones, the top 2 antibody expressing clones were then expanded into spinner flasks for growth and productivity comparison to select the highest antibody expressing clone. A stable clone (Clone #19) that expressed approximately 418 mg/L human IgG (17.356 p/c/d specific productivity) was identified (FIGS. 2 and 3) and used to prepare a cell bank. Copy number analysis by quantitative polymerase chain reaction ("qPCR") of the amplifiable marker gene showed an increase in the gene copy number from approximately 100 copies per cell to approximately 200 copies per cell.

Example 2

Three clones of a CHO cell line transfected with a nucleic acid sequence encoding human IgG and a nucleic acid sequence encoding the amplifiable marker DHFR were passaged in MTCM media with 500 nM of the amplification agent MTX. An equal number of cells from each clone were pooled (pre-amplification pool) and this mixture was inoculated into a five liter perfusion bioreactor in animal component free medium.

Figure 4:
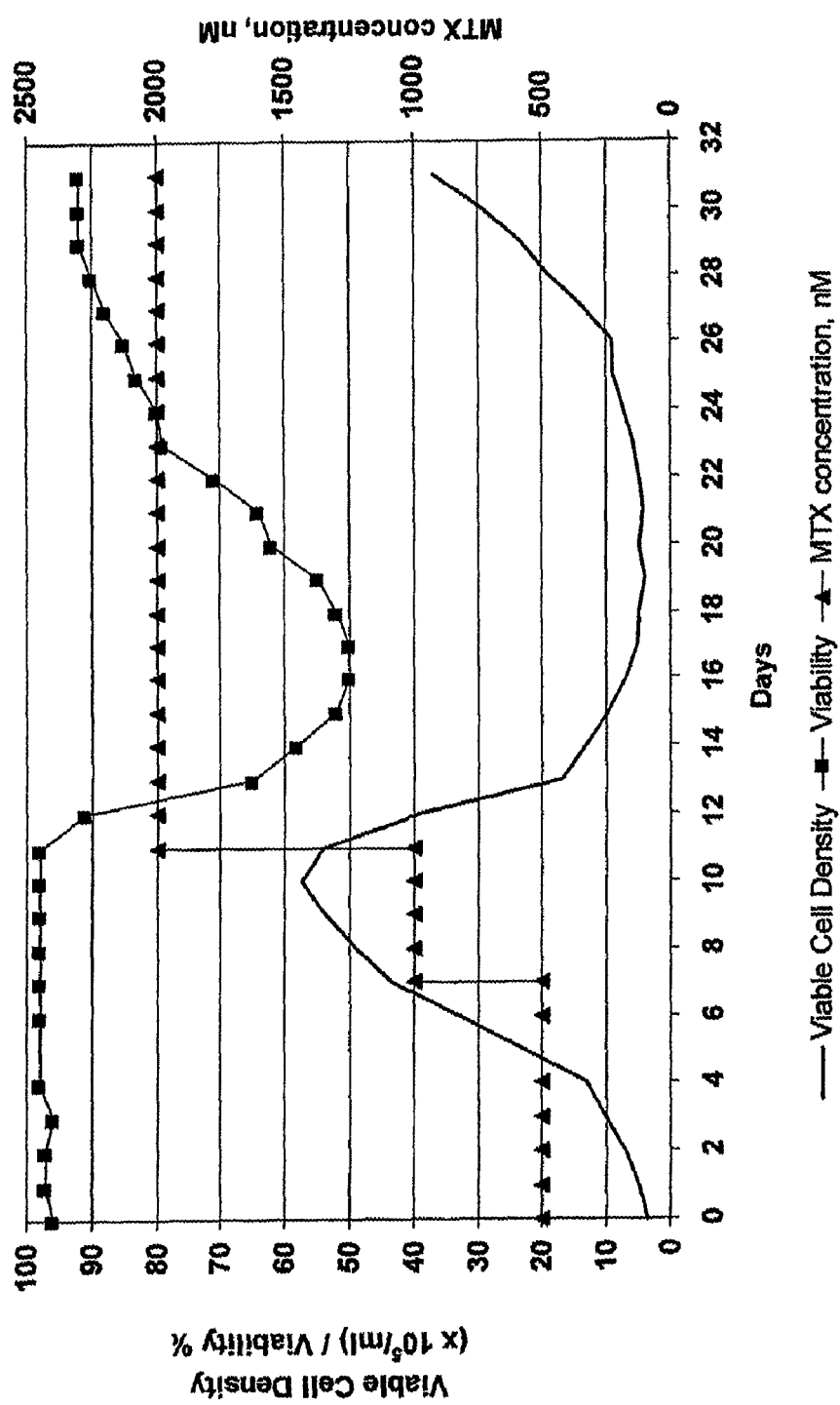
FIG. 4 is a graph illustrating growth, viability, and MTX concentration profiles of host cells amplified in a perfusion bioreactor.
Figure 5:
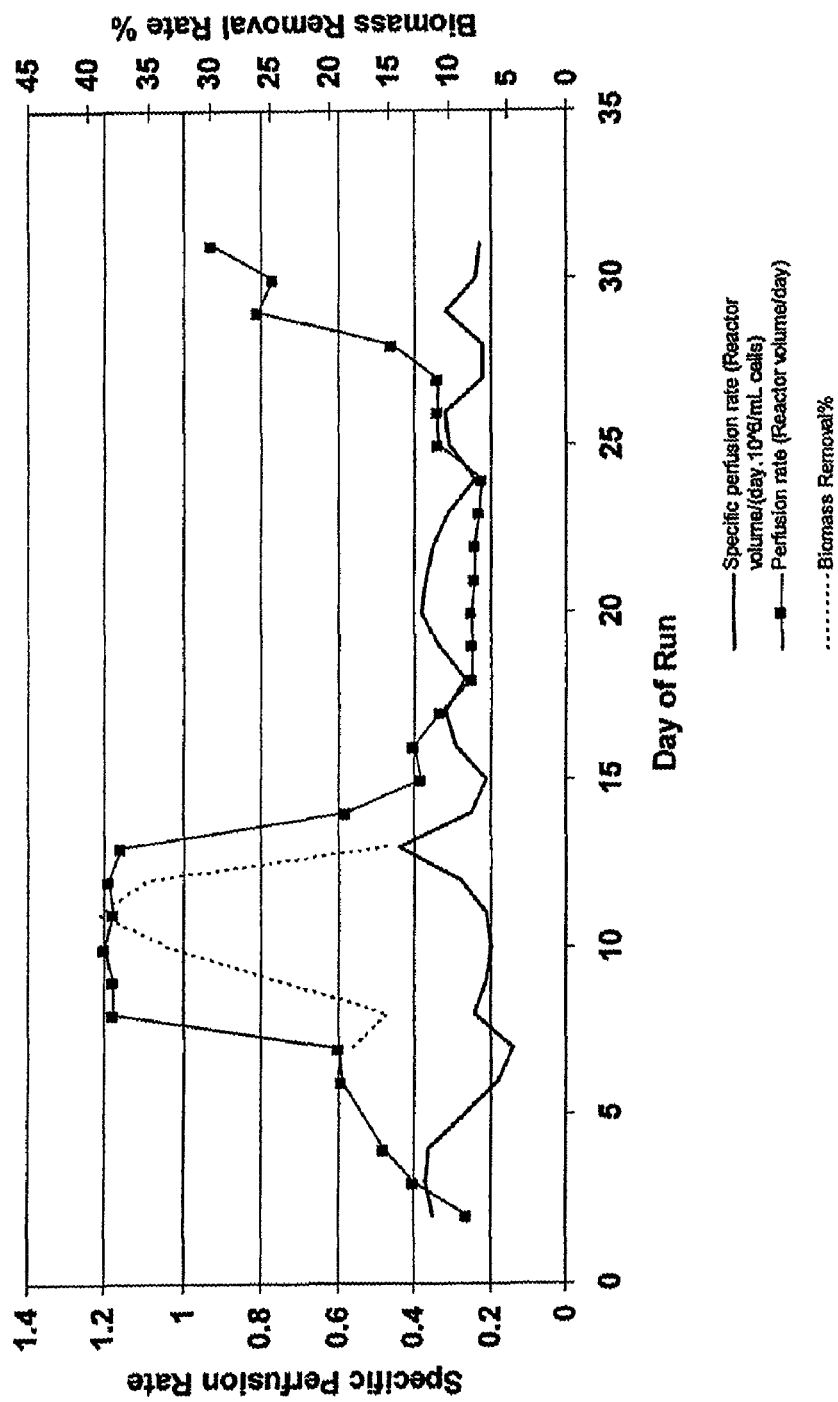
FIG. 5 is a graph illustrating perfusion rate and biomass removal rate in a perfusion amplification bioreactor.

After 6 days, the concentration of the amplification agent, MTX, in the medium was increased from 500 nM to 1000 nM. After 11 days, the concentration of MTX in the medium was increased from 1000 nM to 2000 nM. Development cell banks ("DCB") were prepared at appropriate stages for use in subcloning to isolate higher producing clones. FIGS. 4 and 5 illustrate growth, viability, and MTX concentration profiles of host cells amplified in a perfusion bioreactor.

Figure 6:
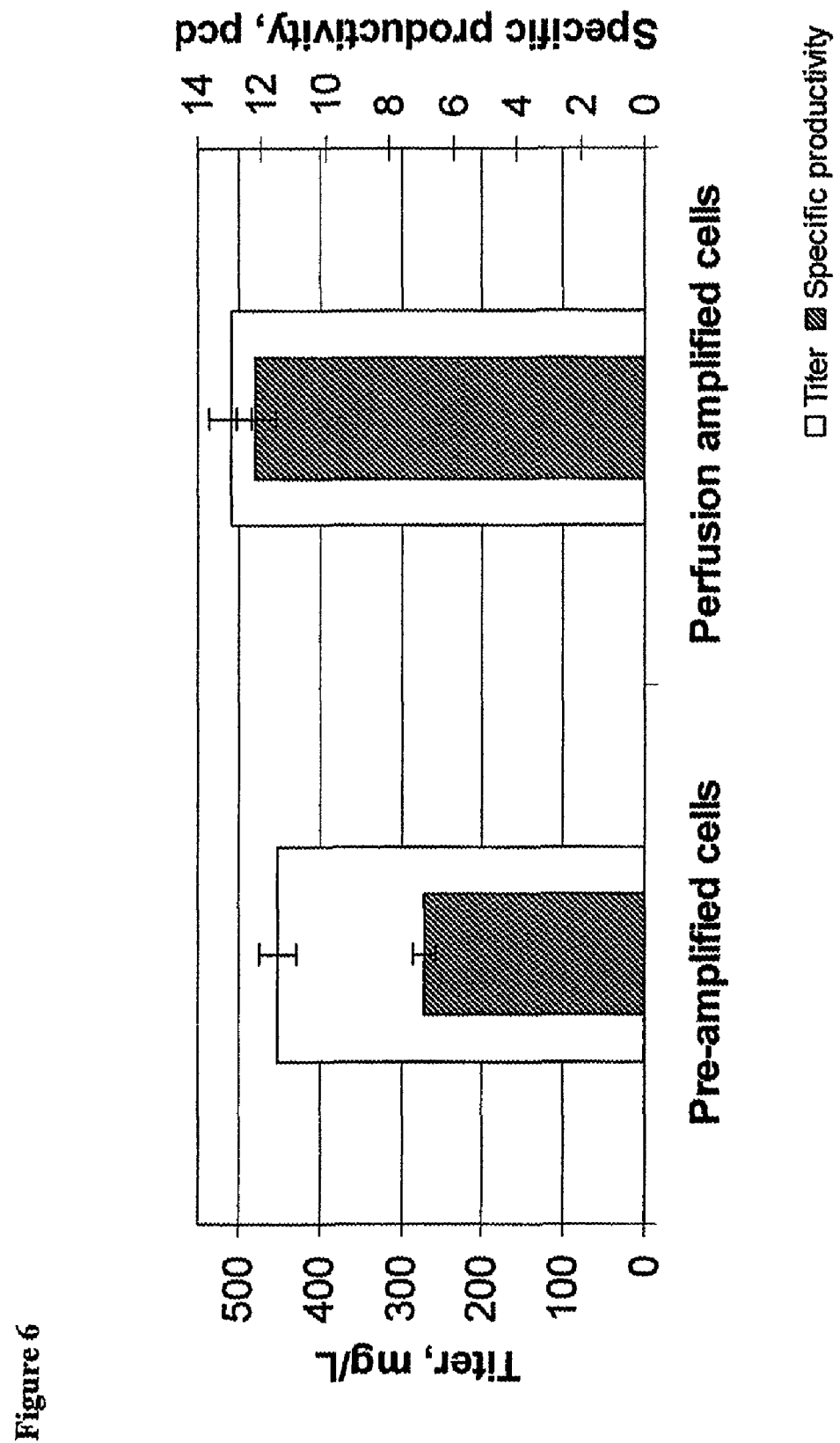
FIG. 6 is a graph illustrating titer and specific productivity of perfusion amplified cells and preamplified pooled cells.

Volumetric and specific productivity differences between preamplified cells and amplified cells are presented in FIG. 6. From these results, it can be observed that there was a 13% increase in volumetric productivity and a 76% increase in specific productivity in the 2000 nM MTX amplified cells.

Figure 7:
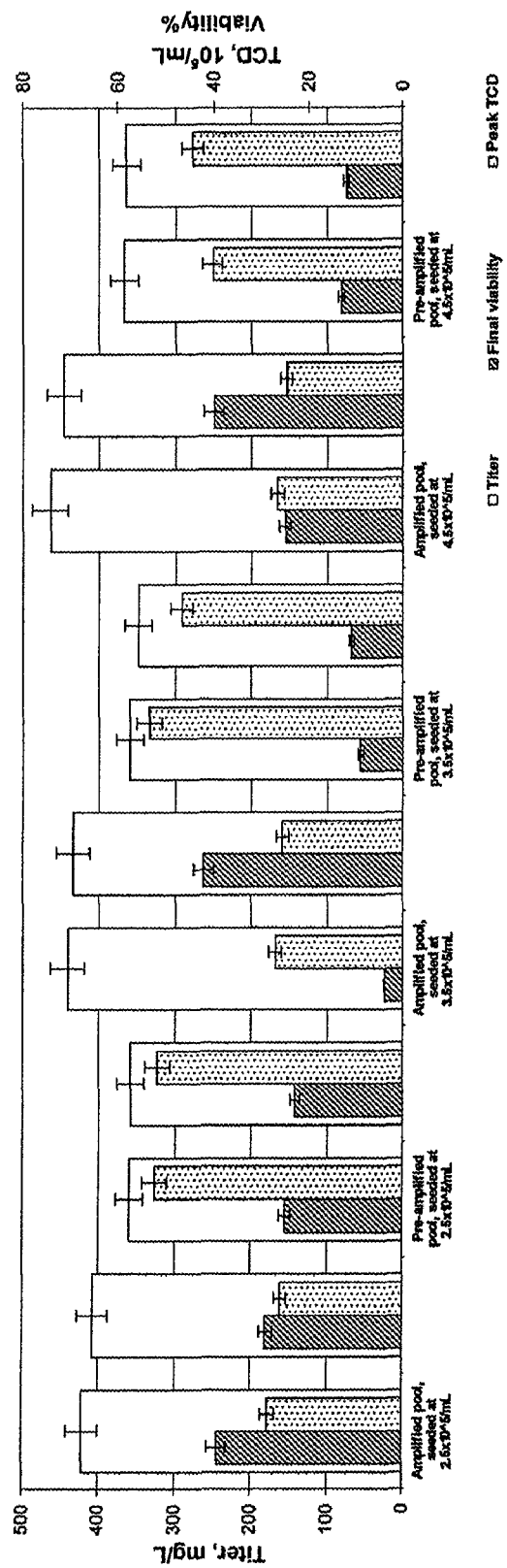
FIG. 7 is a graph illustrating titer and total peak cell densities of perfusion amplified cells and preamplified pooled cells.

In addition, growth studies were performed using the pre-amplified cells and the amplified cells on Day 28 at different seeding densities, 2.5, 3.5 and 4.5×10$^6$ vc/mL in duplicates. See FIG. 7. From these results, it can be observed that there were higher batch titers (16 to 25% increase) and lower total peak cell densities (40 to 50% decrease) after amplification to 2000 nM MTX.

Copy number analysis by qPCR revealed an approximately 17% increase in the gene copy number of human IgG in the 2000 nM MTX amplified cells, suggesting that the amplification by increased MTX concentration correlated with the higher amplifiable marker gene copy number compared to pre-amplified cells. This was also correlated with higher levels of human IgG, suggesting the amplification of the gene for the polypeptide of interest. The results are shown in Table 2 below.

TABLE 2

| Days in bioreactor | Copy Number/cell | Standard Deviation | % Change |
|---|---|---|---|
| Pre-amplified pool | 17.86 | 0.13 | REF |
| 11 | 19.94 | 0.24 | 12 |
| 25 | 20.87 | 0.15 | 17 |
| Clone #53 from Day 25 | 34.7 | 0.5 | 94 |
| Clone #16 from Day 25 | 34.6 | 1.7 | 94 |

Note:
copy number analysis for Clone #53 and Clone #16 were run on a different day.

Figure 8:
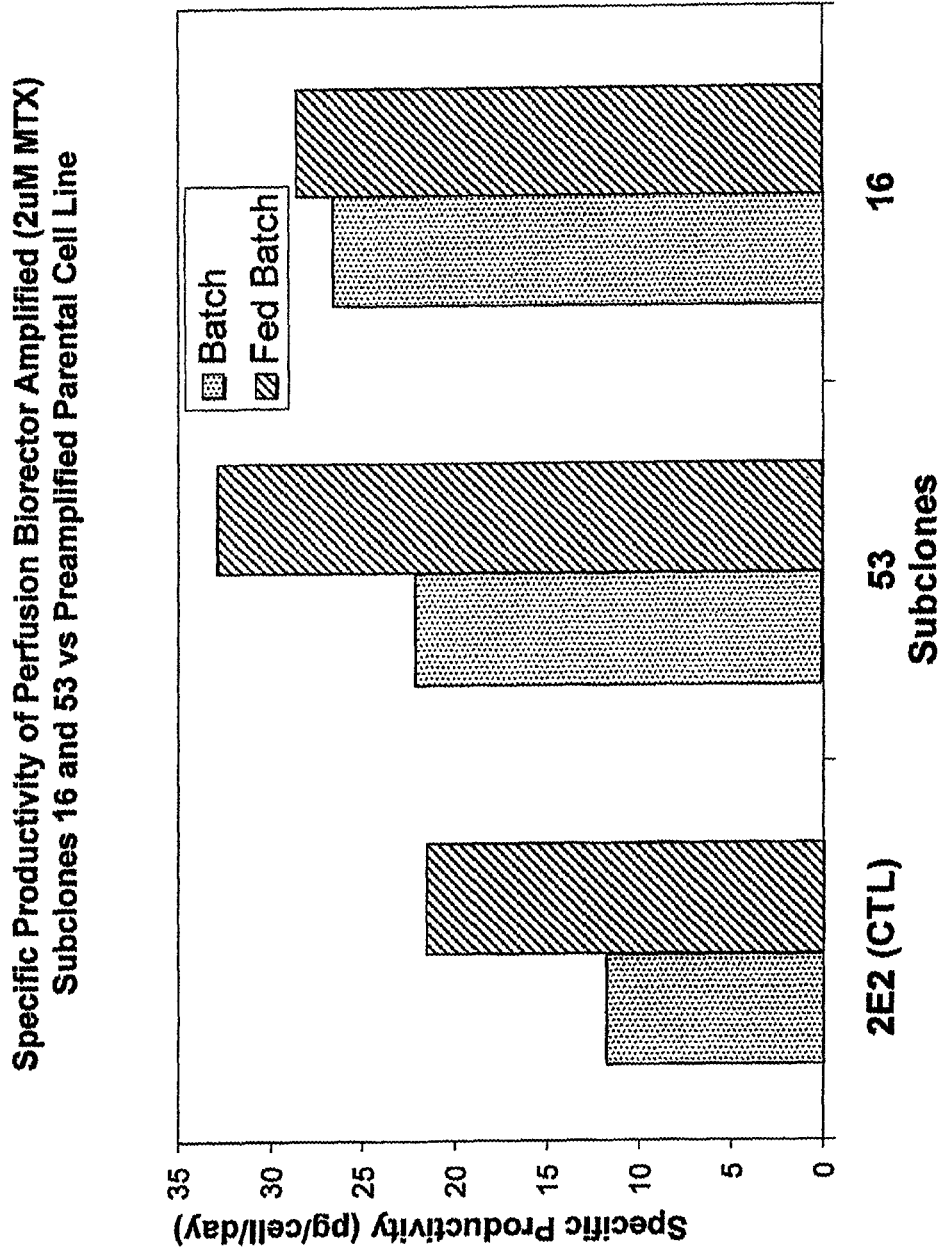
FIG. 8 is a graph illustrating specific productivity from perfusion amplified cell lines and preamplified cell line.

Additionally, 2000 nM MTX amplified cells were subcloned for higher expressors and these subclones showed improved specific productivity compared to the 500 nm MTX resistant cells. See FIG. 8.

Copy number analysis by qPCR revealed an approximately 94% increase in the gene copy numbers of 2000 nM MTX amplified subclones. This was correlated with higher levels of human IgG, suggesting the amplification of the gene for the polypeptide of interest. The results are shown in Table 2 above.

Example 3

Bulk-transfected CHO cells (i.e., bulk transfectants, which are not single cell clones) with a nucleic acid sequence encoding human IgG and a nucleic acid sequence encoding the amplifiable marker DHFR were passaged in MTCM media with 50 nM of the amplification agent MTX. Cells were inoculated into a five liter perfusion bioreactor in animal component free medium for further amplification.

Figure 9:
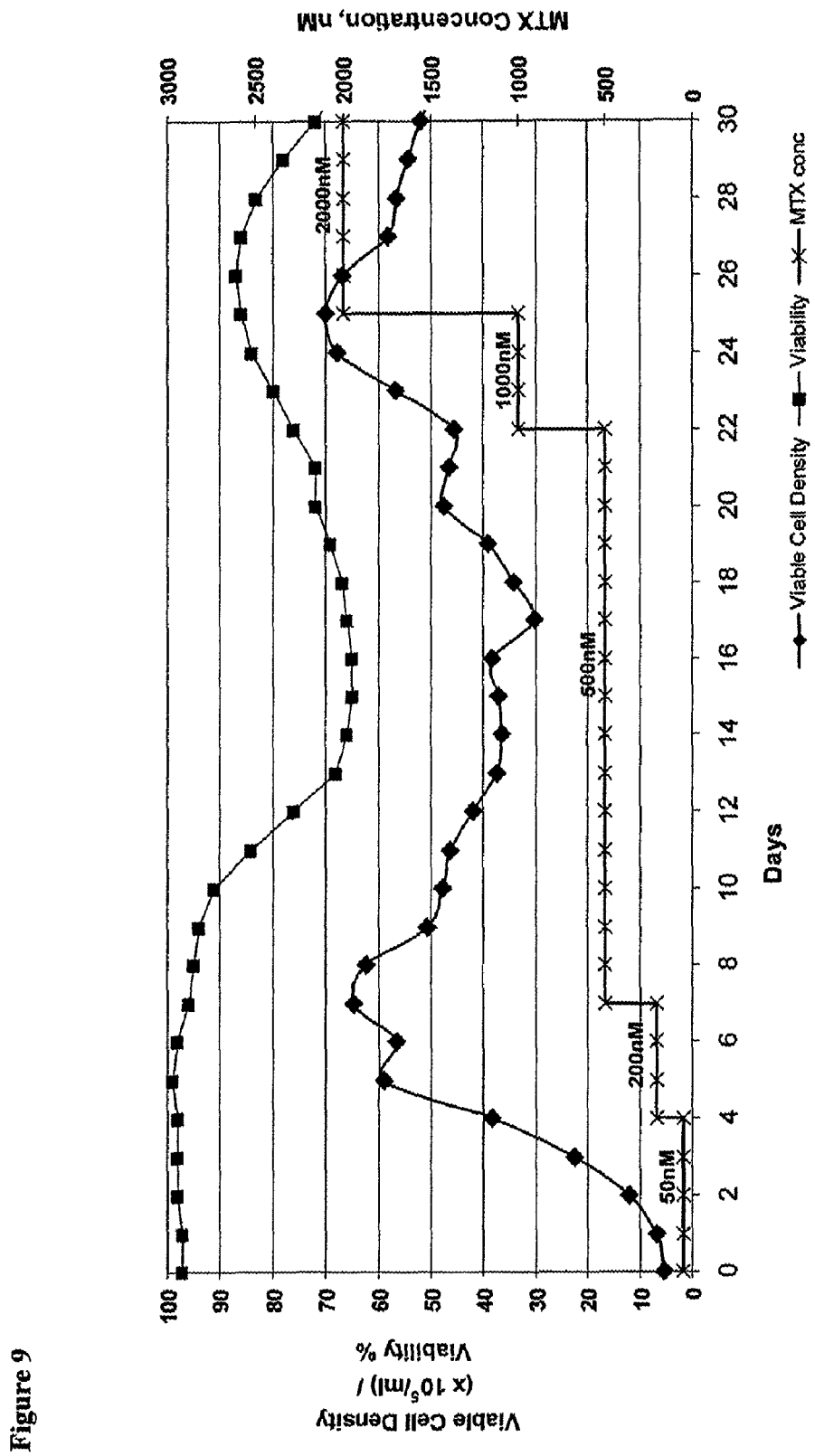
FIG. 9 is a graph illustrating growth, viability, and MTX concentration profiles of bulk transfected cells amplified in a perfusion bioreactor.

After 4 days, the concentration of the amplification agent MTX in the medium was increased from 50 nM to 200 nM. After another 3 days, the concentration of MTX in the medium was increased from 200 nM to 500 nM. After 15 days, the concentration of MTX in the medium was increased from 500 nM to 1000 nM, and 3 days later the MTX concentration was increased to 2000 nM. Development cell banks ("DCB") were prepared at appropriate stages for subcloning to isolate higher producing clones. FIG. 9 illustrates growth, viability, and MTX concentration profiles of CHO cells amplified in a perfusion bioreactor.

Copy number analysis by qPCR revealed an approximately 180% increase in the gene copy number of human IgG in the 1000 nM and 2000 nM MTX amplified cells This suggests that the amplification by increased MTX concentration correlated with the higher amplifiable marker gene copy number compared to pre-amplified cells, as well as amplification of the gene for the polypeptide of interest. The results are shown in Table 3 below.

TABLE 3

Copy number analysis results

| Days in bioreactor | Heavy Chain (HC) Copy # | Std. Dev. | % change from Ref (HC) | Light Chain (LC) Copy # | Std. Dev. | % change from Ref (LC) |
|---|---|---|---|---|---|---|
| Pre-amplified pool | 4.0 | 0.2 | Ref | 3.4 | 0.5 | Ref |
| 25 | 9.9 | 0.3 | 147.5 | 9.4 | 0.6 | 176.5 |
| 28 | 10.0 | 0.1 | 150 | 9.8 | 0.5 | 188.2 |

The contents of all issued patents, patent applications, and publications identified in this application, including any and all priority applications of the instant application, are hereby expressly incorporated by reference in their entirety.

What is claimed is:

1. A method for producing a recombinant cell line that highly expresses a polypeptide of interest, comprising:
    (a) inoculating host cells in a perfusion bioreactor, wherein the host cells are transfected with (i) a nucleic acid sequence encoding a polypeptide of interest and (ii) a nucleic acid sequence encoding an amplifiable marker;
    (b) culturing the host cells in the presence of an increasing amount of an amplification agent in the perfusion bioreactor to amplify the nucleic acid sequence encoding a polypeptide of interest in the host cells; and
    (c) subcloning the host cells from (b) to produce a cell line that highly expresses a polypeptide of interest.

2. The method of claim 1 wherein the nucleic acid sequence encoding a polypeptide of interest and the nucleic acid sequence encoding an amplifiable marker are contained on a single vector.

3. The method of claim 1 wherein the amplifiable marker encodes a DHFR protein.

4. The method of claim 1 wherein the host cells are mammalian cells.

5. The method of claim 1 wherein the host cells are CHO cells.

6. The method of claim 1 wherein the polypeptide of interest is an antibody.

7. The method of claim 1 wherein the increasing amount of the amplification agent is added to the media when % cell viability is increasing or stable.

8. The method of claim 1, wherein the host cells are derived from the same single clone.

9. The method of claim 1, wherein the host cells are pooled multiple clones.

10. The method of claim 1, wherein the host cells are bulk transfectants.

11. The method of claim 1, wherein the amplification agent is methotrexate.

* * * * *

UNITED STATES PATENT AND TRADEMARK OFFICE
CERTIFICATE OF CORRECTION

PATENT NO.        : 8,357,514 B2  
APPLICATION NO.   : 12/593132  
DATED             : January 22, 2013  
INVENTOR(S)       : Arunakumari et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 374 days.

Signed and Sealed this  
Thirteenth Day of May, 2014

Michelle K. Lee  
*Deputy Director of the United States Patent and Trademark Office*